US005157203A

United States Patent [19]
Brown et al.

[11] Patent Number: 5,157,203
[45] Date of Patent: Oct. 20, 1992

[54] SEPARATION OF ORGANIC SULFIDES FROM OLEFINS

[75] Inventors: Ronald E. Brown, Bartlesville, Okla.; Ted H. Cymbaluk, Seabrook, Tex.

[73] Assignee: Phillips Petroleum Company, Bartlesville, Okla.

[21] Appl. No.: 827,183

[22] Filed: Jan. 28, 1992

[51] Int. Cl.$^5$ .................. C07C 7/148; C07C 7/00; C01B 17/00
[52] U.S. Cl. .................. 585/845; 585/833; 585/856; 585/864; 423/243; 423/245.1; 423/245.2; 423/242.2; 423/243.07
[58] Field of Search .............. 585/833, 845, 856, 866, 585/864; 423/242, 243, 245.1, 245.2

[56] References Cited

U.S. PATENT DOCUMENTS

| | | | |
|---|---|---|---|
| 2,496,536 | 2/1950 | Hoover | 196/28 |
| 2,503,627 | 4/1950 | McBride et al. | 196/30 |
| 2,653,125 | 9/1953 | Krause | 196/29 |
| 2,975,200 | 3/1961 | Warner | 260/439 |
| 3,008,870 | 11/1961 | Mailen et al. | 167/22 |
| 3,206,465 | 9/1965 | Reifschneider | 260/299 |
| 3,420,862 | 1/1969 | Long | 260/438.1 |
| 3,595,928 | 7/1971 | Rideout et al. | 260/654 S |
| 3,647,840 | 3/1972 | Bills | 260/438.1 |
| 3,763,200 | 10/1973 | Dines | 585/845 |
| 4,025,574 | 5/1977 | Tabler et al. | 260/677 A |
| 4,042,669 | 8/1977 | Johnson et al. | 423/246 |
| 4,129,605 | 12/1978 | Tabler et al. | 260/669 A |
| 4,398,052 | 8/1983 | Tabler et al. | 585/845 |
| 4,400,564 | 8/1983 | Johnson et al. | 585/845 |

OTHER PUBLICATIONS

"Comprehensive Inorganic Chemistry", vol. 3, J. C. Bailar et al., Pergamon Press, 1973, pp. 29, 30, 34 and 40.

Primary Examiner—Anthony McFarlane
Assistant Examiner—Nhat Phan
Attorney, Agent, or Firm—K. K. Brandes

[57] ABSTRACT

Organic sulfides are separated from olefins (in particular monoolefins) by absorption with Cu(I) salt(s) of a hydrocarbonsulfonic acid, preferably a solution of Cu(I) dodecylbenzene sulfonate(s).

17 Claims, 1 Drawing Sheet

SEPARATION OF ORGANIC SULFIDES FROM OLEFINS

BACKGROUND OF THE INVENTION

This invention relates to the separation of organic sulfides from olefin-containing fluids. In a particular aspect, this invention relates to the removal of organic sulfide impurities from monoolefin-containing gases.

The presence of organic sulfides in olefin streams, in particular monoolefin streams which are used as feeds for polymerization processes, is undesirable for a variety of reasons, e.g., because the sulfides can act as catalyst poisons. This invention is directed to an effective process for absorbing organic sulfides from olefin-containing fluids, in particular monoolefin-containing gases.

SUMMARY OF THE INVENTION

It is an object of this invention to separate organic sulfides from olefins, in particular monoolefins. It is another object of this invention to remove organic sulfide impurities from monoolefin-containing gases. Other objects will become apparent from the detailed description and the appended claims.

In accordance with this invention, a process for separating organic sulfides from olefins comprises:

contacting a fluid feed comprising at least one olefin (i.e., one or two or more olefins) containing 2-6 carbon atoms per molecule and at least one organic sulfide of the formula R-S-R', wherein R and R' are independently selected from the group consisting of alkyl, cycloalkyl and aryl groups containing 1-10 carbon atoms with an absorbent composition comprising at least one copper(I) salt of a hydrocarbonsulfonic acid, under such contacting conditions as to obtain a fluid product containing said at least one organic sulfide at a lower concentration than said fluid feed.

In one preferred embodiment, the alkyl groups R and R' of the organic sulfide(s) are alkyl groups. In another preferred embodiment, the feed contains at least one gaseous monoolefin. In a further preferred embodiment, the feed contains at least one organic sulfide at such a level as to provide a sulfur content in said feed of less than about 1 weight-% S. In still another preferred embodiment, the absorbent composition comprises a solution of at least one copper(I) salt of a hydrocarbonsulfonic acid in an organic solvent.

BRIEF DESCRIPTION OF THE DRAWING

The FIGURE depicts a preferred process for absorbing organic sulfide impurities from a gaseous monoolefin stream and the regeneration of the spent absorbent solution.

DETAILED DESCRIPTION OF THE INVENTION

Figure 1:
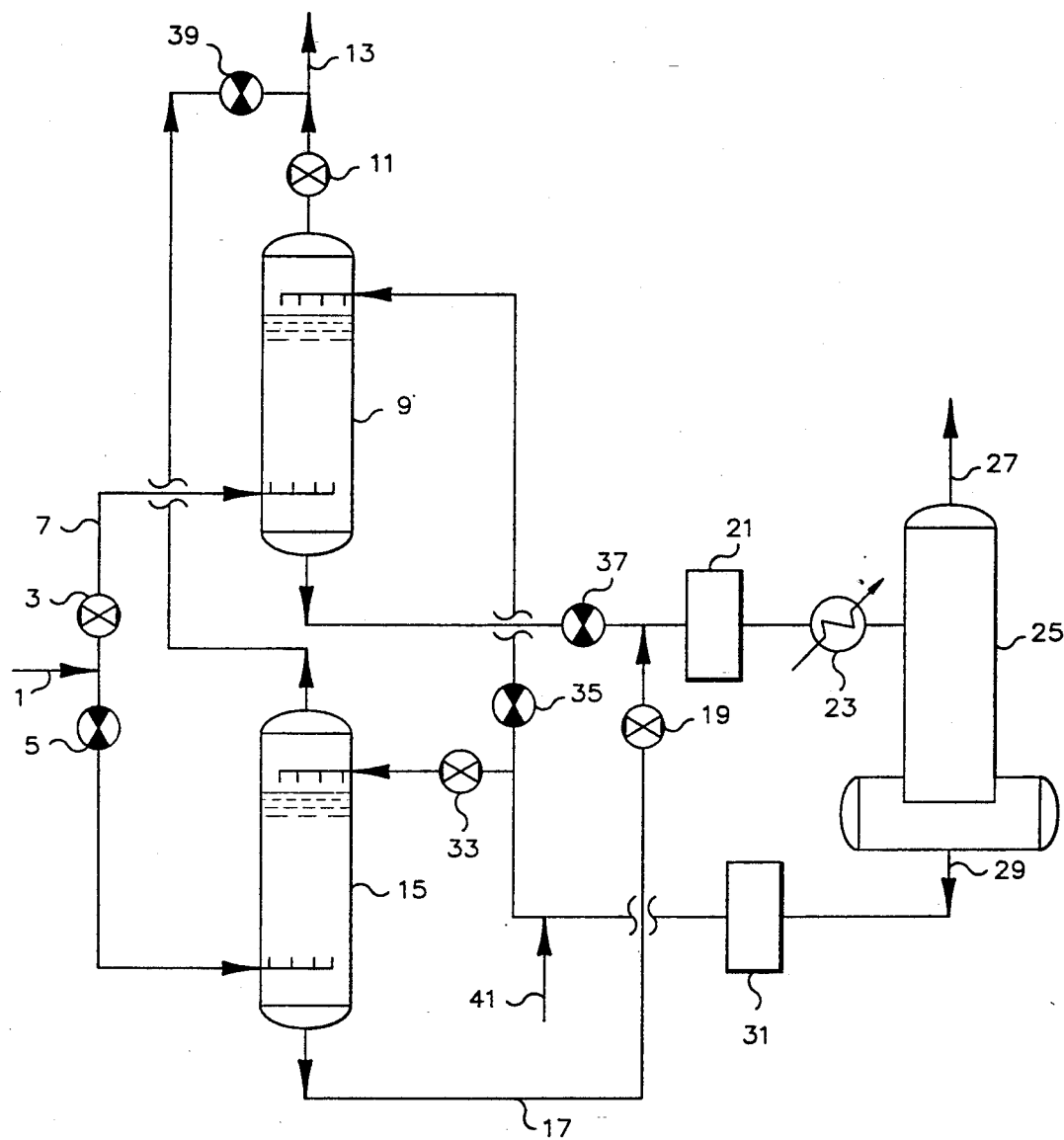

Any suitable olefin-containing fluid feed which also contains organic sulfide(s) can be employed as a feed in the process of this invention. The feed fluid can be liquid or gaseous, preferably gaseous. The olefins contained in the feed can be monoolefins and/or diolefins, preferably monoolefins (alkenes), more preferably ethylene, propylene, butene-1, butene-2, isobutene, and mixtures thereof. Non-limiting examples of organic sulfides contained in the feed include dimethyl sulfide, methyl ethyl sulfide (presently preferred), diethyl sulfide, ethyl propyl sulfide, dipropyl sulfides, propyl butyl sulfides, dibutyl sulfides, and mixtures thereof. The feed may (but preferably does not) contain impurities such as $H_2S$, mercaptans, carbon monoxide and arsines which can also react with the sorbent composition. The concentration of these additional impurities which may be present in the feed should be low enough so that they do not significantly interfere with the absorption process of this invention.

Preferably, the feed is gaseous at ambient conditions (about 25° C., 1 atm.), and the monoolefin content in the feed is in the range of about 99 to about 99.999 weight-%. Also preferably, the content of the organic sulfide impurities in the feed is such as to provide a sulfur content in the range of about 0.1 to about 1000 ppm S (i.e., about 0.1–1,000 parts by weight of sulfur per 1 million parts of the feed).

Any suitable copper(I) salt of a hydrocarbonsulfonic acid can be employed as a sorbent material in the process of this invention. Preferred copper(I) salts of hydrocarbonsulfonic acids are those disclosed in U.S. Pat. No. 4,400,564, and include copper(I) salts of alkanesulfonic acids containing 4-20 carbon atoms per molecule and of aromatic sulfonic acids containing 6-22 carbon atoms per molecule.

The copper(I) salts of alkanesulfonic acids useful in the practice of this invention can be those of straight-chain or branched alkanesulfonic acids. Non-limiting examples of suitable copper(I) salts of alkanesulfonic acids include copper(I) salts of n-butanesulfonic acid, 2-ethyl-1-hexanesulfonic acid. 2-methyl-1-nonanesulfonic acid, n-dodecanesulfonic acid, 2-ethyl-5-n-octyl-decanesulfonic acid, n-eicosanesulfonic acid, and mixtures thereof.

Non-limiting examples of copper(I) salts of aromatic sulfonic acids useful in the practice of this invention include copper(I) salts of benzenesulfonic acid, alkylbenzenesulfonic acids wherein the alkyl member contains from 1 to 16 carbon atoms, such as p-toluenesulfonic acid, p-dodecylbenzenesulfonic acid, p-hexadecylbenzenesulfonic acid, and the like, naphthalenesulfonic acid, phenolsulfonic acid, naphtholsulfonic acids and halogenbenzenesulfonic acids, such as p-chlorobenzenesulfonic acid, p-bromobenzenesulfonic acid, and mixtures thereof. Presently preferred is at least one copper(I) salt of dodecylbenzenesulfonic acid (including mixtures of copper(I) salts of o-, m-, and p-dodecylbenzenesulfonic acids). More preferably, the absorbent is the copper(I) salt of para-dodecylbenzenesulfonic acid.

Copper(I) salts of petroleum sulfonic acids which comprise copper(I) salts of various alkanesulfonic acids and aromatic sulfonic acids can also be used in the practice of this invention. Petroleum sulfonic acids can be prepared by sulfonation, generally with an $SO_3/SO_2$ mixture, of a deasphalted solvent-refined petroleum fraction having a viscosity of about 140–720 SUS at 210° F.

The copper(I) salts of hydrocarbonsulfonic acids (also referred to as copper(I) hydrocarbonsulfonates) used as sorbents in the present invention are generally prepared by refluxing a solution of the corresponding sulfonic acid in a suitable diluent, preferably xylene(s), together with cuprous oxide, with a provision for removing the water of reaction, as has been described in U.S. Pat. No. 4,400,564. The preparation is generally carried out in an oxygen-free inert atmosphere, such as under nitrogen, preferably at a molar ratio of sulfonic acid to copper of about 1:1, for a period of time sufficient to substantially complete the reaction. If desired, the formed copper salt can be separated from the diluent, such as by vacuum distillation.

The copper(I) hydrocarbon sulfonate sorbent can be applied in solid form, e.g., in a fixed sorbent bed. But this procedure is presently not preferred. Generally, the copper(I) sulfonate is dissolved in a suitable hydrocarbon solvent, preferably at least one aromatic hydrocarbon solvent containing 6–15 carbon atoms per molecule, to produce a solution of the absorbent material. Examples of suitable aromatic solvents include benzene, the alkyl derivatives of benzene, such as toluene, xylene isomers, isopropylbenzene, 1,3,5-trimethylbenzene, hexamethylbenzene, halogen-substituted benzenes, polynuclear aromatic hydrocarbons such as naphthalene, methylnaphthalenes and the like and mixtures thereof. It is also possible to employ an aromatic hydrocarbon containing mixture, such as light cycle oil, as solvent. The aromatic solvents which are presently more preferred are xylene(s), i.e., ortho- or meta- or para-xylene, or a mixture of two or three xylenes (at any suitable ratio). Generally, the concentration of the dissolved copper(I) hydrocarbonsulfonate(s) in the sorbent solution is about 0.05–2 mole/l, preferably about 0.1–1.5 mole/l.

Any suitable contacting conditions can be employed in the sorption process of this invention. Generally, the temperature in the contacting zone is in the range of from about $-20°$ to about $100°$ C., preferably about $20°$ to about $50°$ C. Generally, the pressure in the contacting zone is in the range of from about 1 to about 70 atm. When a solid sorbent material is employed, the gas hourly space velocity of the gaseous feed in the contacting zone generally is in the range of from about 10 to about 20,000 volume of feed/volume of sorbent/hour, measured at about $25°$ C./1 atm. When a dissolved sorbent (i.e., a solution of a copper salt of a hydrocarbonsulfonic acid) is employed, the volume ratio of the gaseous feed to the liquid sorbent solution generally is in the range of from about 3:1 to about 500:1 (preferably about 5:1 to about 100:1). Generally, the contacting is continued as long as an adequate degree of organic sulfide removal is attained. The spent sorbent material is preferably regenerated by heating it to a temperature of about $280°-380°$ F. at a pressure of about 0–20 psig so as to remove absorbed organic sulfide(s) therefrom.

Treatment of the feed in accordance with the process of this invention can be carried out in any suitable manner. In one embodiment, a bed of a solid sorbent is placed as a fixed bed in a confined zone, and a fluid stream (preferably a gas) is passed therethrough in either upward or downward flow. Other suitable methods of treatment include a fluidized operation in which the feed and the solid sorbent particles are maintained in a state of turbulence under hindered settling conditions in a confined zone, or a moving bed operations in which the solid sorbent passes as a moving bed concurrently with the feed. In a fixed bed operation of a continuos process, the flow of fluid can be rotated between two or more sorbent beds, with at least one being operated in an absorption mode and the other being in a regeneration (desorption) mode. Continuous processes are preferred, but it is understood that batch type operations can be employed when desired.

When a solution of a dissolved sorbent is employed, the gaseous feed and the liquid sorbent solution are generally contacted in a continuous countercurrent absorption column (well known to those skilled in the art) wherein the gaseous feed generally flows upward and the sorbent solution flows downward. In another (presently preferred) embodiment, the gaseous feed is sparged through the sorbent solution in an absorption vessel so as to provide intimate contact between the feed gas and the dissolved sorbent. The feed gas flow can be rotated between two absorption columns or vessels, with one being operated in an absorption mode and the other one being in the regeneration (desorption) mode.

The process of this invention will be further illustrated by the following non-limiting examples.

EXAMPLE I

This example illustrates the experimental setup for investigating the removal of an organic sulfide from a monoolefin stream by means of a dissolved copper(I) salt of a hydrocarbonsulfonic acid.

The employed sorbent was a 0.4 molar solution of copper(I) p-dodecylbenzenesulfonate (prepared substantially in accordance with the procedure of Example I of U.S. Pat. No. 4,400,564) in xylene. A propylene feed stream which contained methyl ethyl sulfide at a level of 102 ppm sulfur was bubbled through 75 cc of the above-described sorbent solution at a rate of 700 cc feed gas per minute. The exiting product gas contained only 7 ppm sulfur. Thus, a 93% sulfide removal rate was achieved by the process of this example.

EXAMPLE II

This example illustrates a preferred organic sulfide absorption/desorption operation, as depicted in the FIGURE. Pumps, control devices and other standard operating equipment are not shown.

A feed gas which contains ethylene (or another gaseous monoolefin) and organic sulfide impurities is introduced through conduit 1, open valve 3 and conduit 7 into absorption vessel 9 containing a copper(I) hydrocabonsulfonate solution. The feed gas is sparged through the solution which absorbs organic sulfur impurities. The purified monoolefin product gas (from which a substantial portion of organic sulfide impurities has been removed) exits through open valve 11 and conduit 13.

Meanwhile, a second absorption vessel (vessel 15) is operated in a desorption mode. Spent sorbent solution (i.e., Cu(I) hydrocarbonsulfonate solution containing absorbed organic sulfide impurities) is pumped from vessel 15 through conduit 17, open valve 19, filter 21 and heat exchanger 23 (where the spent sorbent solution is heated to a temperature of about $330°$ F.) into desorption column 25 (which may contain trays or Rasching rings or the like). The desorbed organic sulfide exits through conduit 27. The regenerated sorbent solution is pumped through conduit 29, filter 31 and open valve 33 back into vessel 15. Valves 5, 35, 37 and 39 are closed. If desired, fresh copper(I) hydrocarbonsulfonate solution is introduced through conduit 41 (to replace lost solvent and Cu(I) hydrocarbonsulfonate). The desorption process is continued until the organic sulfide content of the regenerated sorbent solution in vessel 15 is substantially nil.

Thereafter, vessel 15 is operated in the absorption mode and vessel 9 is operated in the regeneration mode by closing valves 3, 11, 19 and 33, and opening valves 5, 35, 37 and 39.

Reasonable variations, modifications and adaptations for various usages and conditions can be made within the scope of the disclosure and the appended claims, without departing from the scope of this invention.

That which is claimed is:

1. A process for separating organic sulfides from olefins comprising
   contacting a fluid feed comprising at least one olefin containing 2-6 carbon atoms per molecule and at least one organic sulfide of the formula R—S—R', wherein R and R' are independently selected from the group consisting of alkyl, cycloalkyl and aryl groups containing 1-10 carbon atoms
   with an absorbent composition comprising at least one copper(I) salt of a hydrocarbon sulfonic acid,
   under such contacting conditions as to obtain a fluid product containing said at least one organic sulfide at a lower concentration than said fluid feed.

2. A process in accordance with claim 1, wherein said feed and said product are gaseous.

3. A process in accordance with claim 1, wherein said at least one olefin is at least one monoolefin.

4. A process in accordance with claim 3, wherein said at least one monoolefin is selected from the group consisting of ethylene, propylene, butene-1, butene-2 and isobutene.

5. A process in accordance with claim 1, wherein R and R' in said at least one organic sulfide are alkyl groups.

6. A process in accordance with claim 5, wherein said at least one organic sulfide is selected from the group consisting of dimethyl sulfide, methyl ethyl sulfide, diethyl sulfide, ethyl propyl sulfides, dipropyl sulfides, propyl butyl sulfides, and dibutyl sulfides.

7. A process in accordance with claim 1, wherein the content of said at least one organic sulfide in said feed is such as to provide a level of about 0.1 to about 1,000 ppm sulfur.

8. A process in accordance with claim 1, wherein said at least one copper(I) salt of hydrocarbonsulfonic acid is selected from the group consisting of copper(I) salts of alkanesulfonic acids containing 4-20 carbon atoms per molecule and copper(I) salts of aromatic sulfonic acids containing 6-22 carbon atoms per molecule.

9. A process in accordance with claim 8, wherein said at least one copper(I) salt of a hydrocarbonsulfonic acid is at least one copper(I) salt of dodecylbenzenesulfonic acid.

10. A process in accordance with claim 1, wherein said absorbent composition is a solution of at least one copper(I) salt of a hydrocarbonsulfonic acid.

11. A process in accordance with claim 1, wherein said absorbent composition is a solution of at least one copper(I) salt of an aromatic sulfonic acid containing 6-22 carbon atoms per molecule in at least one aromatic hydrocarbon containing 6-15 carbon atoms per molecule.

12. A process in accordance with claim 11, wherein said at least one copper(I) salt of an aromatic sulfonic acid is at least one copper(I) salt of a dodecylbenzenesulfonic acid, and said at least one aromatic hydrocarbon is at least one xylene.

13. A process in accordance with claim 11 wherein the concentration of said at least one copper(I) salt of an aromatic sulfonic acid is about 0.05-2 mole/liter.

14. A process in accordance with claim 1, wherein said feed is gaseous, said absorbent compositions is a solution of at least one copper(I) salt of a hydrocarbonsulfonic acid, and the volume ratio of said feed to said absorbent composition is about 3:1 to about 500:1.

15. A process in accordance with claim 1, wherein said contacting conditions comprise a temperature in the range of about $-20°$ to about $100°$ C.

16. A process in accordance with claim 1, wherein said fluid feed is gaseous, and said contacting conditions comprise a temperature in the range of about $-20°$ about $100°$ C. and a pressure in the range of about 1 to about 70 atm.

17. A process in accordance with claim 1 comprising the additional step of regenerating spent absorbent composition by heating it to a temperature of about $280°-380°$ F. at a pressure of about 0-20 psig.

* * * * *